United States Patent
Esposito (10) Patent No.: US 7,753,906 B2
(45) Date of Patent: Jul. 13, 2010

(54) CATHETER HAVING ANCHORING AND STABILIZING DEVICES

(76) Inventor: Richard Esposito, 16 Spruce St., Bedminster, NJ (US) 07921

(*) Notice: Subject to any disclaimer, the term of this patent is extended or adjusted under 35 U.S.C. 154(b) by 1217 days.

(21) Appl. No.: 10/941,643

(22) Filed: Sep. 14, 2004

(65) Prior Publication Data
US 2006/0058598 A1    Mar. 16, 2006

(51) Int. Cl.
*A61B 18/18* (2006.01)
(52) U.S. Cl. ............... 606/41; 606/49; 604/101.01; 600/374
(58) Field of Classification Search ........... 607/96, 607/101–107, 113, 122; 600/374–375, 381; 606/41, 46; 604/104, 105, 107, 108, 101.01
See application file for complete search history.

(56) References Cited

U.S. PATENT DOCUMENTS

| | | | |
|---|---|---|---|
| 3,799,172 A | 3/1974 | Szpur | |
| 4,781,682 A | 11/1988 | Patel | |
| 4,808,163 A | 2/1989 | Laub | |
| 5,215,103 A * | 6/1993 | Desai | 606/46 |
| 5,231,995 A * | 8/1993 | Desai | 607/123 |
| 5,324,284 A * | 6/1994 | Imran | 606/15 |
| 5,365,926 A | 11/1994 | Desai | |
| 5,391,199 A | 2/1995 | Ben-Haim | |
| 5,443,449 A | 8/1995 | Buelna | |
| 5,443,489 A | 8/1995 | Ben-Haim | |
| 5,480,422 A | 1/1996 | Ben-Haim | |
| 5,546,951 A | 8/1996 | Ben-Haim | |
| 5,558,091 A | 9/1996 | Acker et al. | |
| 5,702,365 A | 12/1997 | King | |
| 5,851,171 A * | 12/1998 | Gasson | 600/3 |
| 5,855,565 A | 1/1999 | Bar-Cohen et al. | |
| 5,904,670 A | 5/1999 | Schreiner | |
| 6,014,579 A * | 1/2000 | Pomeranz et al. | 600/374 |
| 6,024,740 A | 2/2000 | Lesh et al. | |
| 6,117,101 A | 9/2000 | Diederich et al. | |
| 6,171,277 B1 | 1/2001 | Ponzi | |

(Continued)

FOREIGN PATENT DOCUMENTS

EP    1 398 056 A1    3/2004

(Continued)

OTHER PUBLICATIONS

European Search Report dated Jan. 24, 2006, for Application No. EP05255489.6.

*Primary Examiner*—Roy D Gibson (57) ABSTRACT

A catheter is provided having anchoring and stabilizing devices adapted to respectively sit in and outside an opening of a tubular region. A sheath covering the catheter body forms the anchoring and stabilizing devices, which sheath comprises slits cut into the sheath creating spines. The spines are radially expanded by distal movement of the sheath relative to the catheter body. Radial expansion of the anchoring device generally anchors the distal end of the catheter inside the tubular region. Radial expansion of the stabilizing assembly generally stabilizes the distal end of the catheter against the ostium of the tubular region. The pressure exerted on the tubular region by the anchoring and stabilizing devices minimizes translational and rotational movement of the distal end of the catheter. Alternatively, the catheter may include a telescoping portion extending from the distal end of the catheter in which the anchoring and stabilizing devices are deployed by movement of a puller wire.

32 Claims, 8 Drawing Sheets

U.S. PATENT DOCUMENTS

| | | |
|---|---|---|
| 6,198,974 B1 | 3/2001 | Webster, Jr. |
| 6,210,407 B1 | 4/2001 | Webster |
| 6,270,490 B1 | 8/2001 | Hahnen |
| 6,325,797 B1 * | 12/2001 | Stewart et al. ............... 606/41 |
| 6,527,737 B2 | 3/2003 | Kaneshige |
| 6,685,734 B1 * | 2/2004 | Valimaa et al. ............ 623/1.11 |
| 6,780,183 B2 | 8/2004 | Jimenez, Jr. et al. |
| 6,917,834 B2 * | 7/2005 | Koblish et al. ............. 607/122 |
| 6,966,908 B2 * | 11/2005 | Maguire et al. .............. 606/41 |
| 6,997,925 B2 * | 2/2006 | Maguire et al. .............. 606/41 |
| 2002/0087208 A1 * | 7/2002 | Koblish et al. ............. 607/113 |
| 2002/0198521 A1 | 12/2002 | Maguire |
| 2004/0059327 A1 | 3/2004 | Jenkins et al. |
| 2005/0107829 A1 * | 5/2005 | Edwards et al. ................ 607/2 |

FOREIGN PATENT DOCUMENTS

| | | |
|---|---|---|
| WO | WO 00/51511 A1 | 9/2000 |
| WO | WO 01/37746 A1 | 5/2001 |

* cited by examiner

CATHETER HAVING ANCHORING AND STABILIZING DEVICES

FIELD OF THE INVENTION

The present invention is directed to a mapping and/or ablation catheter with a multi-spine anchoring device and, more particularly, to a mapping and/or ablation catheter with a multi-spine anchoring device for use in a tubular region in or near the heart.

BACKGROUND OF THE INVENTION

Electrode catheters have been in common use in medical practice for many years. They are used to stimulate and map electrical activity in the heart and to ablate sites of aberrant electrical activity. In use, an electrode is inserted into a major vein or artery, such as the femoral artery, and guided into the chamber of the heart which is of concern. Often, the target area of the heart is a tubular region, such as the pulmonary vein, the coronary sinus, the superior vena cava and the inferior vena cava.

Electrode catheters are used to identify and/or ablate tissue in the region of the heart exhibiting the aberrant electrical activity. Often, electrode catheters are capable of both mapping the tissue to locate the site of aberrant electrical activity, and ablating the identified tissue. The ablation of this tissue isolates this tissue from the rest of the heart, thereby preventing the aberrant electrical pathways from extending into other areas of the heart. One area of the heart where such ablation is typically desirable is the pulmonary vein. Several catheters, such as those described in U.S. Pat. Nos. 6,024,740 and 6,117,101, are designed to ablate circumferential lesions inside the pulmonary vein. These catheters comprise an ablation element, such as an ultrasound transducer, surrounded by an inflatable balloon. To ablate the desired circumferential lesion, the balloon is inflated to anchor the catheter within the pulmonary vein, and the transducer is activated to form a circumferential lesion in the tissue engaged by the balloon.

Although they are effective for creating circumferential lesions in heart tissue, these balloon catheters have several disadvantages. For example, the balloon often is situated incorrectly within the pulmonary vein and/or becomes dislodged from the anchoring site. Also, the balloon does not allow blood to flow past it, resulting in a build up of blood at the distal end of the balloon, causing the blood to clot. Accordingly, a mapping and/or ablation catheter having a stabilized anchoring mechanism that enables blood flow and prevents clots is desirable.

SUMMARY OF THE INVENTION

The present invention is directed to a catheter having a catheter body whose distal end has an anchoring device and a stabilizing device that are adapted to respectively sit in and sit outside of an opening of a tubular region, such as an ostium of a pulmonary vein. A sheath covering the catheter body forms the anchoring device and the stabilizing device. In particular, the anchoring device comprises a plurality of slits cut into the sheath where the slits create spines of generally equal length and width in the sheath. Similarly, the stabilizing device comprises a plurality of slits cut into the sheath at a location proximal the anchoring device. The slits create spines of generally equal length and width in the sheath, the spines of the stabilizing device being longer than the spines of the anchoring device.

In one embodiment, the sheath is fixed at its distal end to the distal end of the catheter body. The spines of the anchoring device and the stabilizing device are deployed by distal movement of the sheath relative to the catheter body. Such distal movement of the sheath causes the spines of the anchoring and stabilizing devices to bow outwardly resulting in radial expansion of the anchoring and stabilizing devices. The distal end of catheter body is positioned in or near the heart such that the anchoring device is inside a tubular region, such as the pulmonary vein, and the stabilizing device is proximately and proximally to the ostium outside of the same tubular region. Upon radial expansion of the anchoring device, the spines of the anchoring device exert pressure against the walls of the tubular region thereby generally anchoring the distal end of the catheter body inside the tubular region against proximal and/or radial movement relative to the tubular region. Upon radial expansion of the spines of the stabilizing assembly, the spines of the stabilizing device exert pressure against the ostium of the tubular region thereby generally stabilizing the distal end of the catheter body against distal and/or radial movement relative to the tubular region. Accordingly, the pressure exerted on the walls of the tubular region by the anchoring device and on the ostium by the stabilizing device minimizes, if not prevents, the distal end of the catheter body against both translational and rotational movement. In particular, the pressure exerted on the ostium of the tubular region by the stabilizing device stabilizes the catheter within the heart for delivery of ablation energy to treat the desired area of the heart.

In an alternative embodiment, the distal end of the catheter body has a telescoping portion with a proximal telescoping member and a distal telescoping member. The sheath covers the proximal and distal telescoping members by extending from a distal end of the distal telescoping member to at least a proximal end of the proximal telescoping member. The distal end of the sheath is affixed to the distal end of the distal telescoping member and the proximal end of the sheath is affixed to the distal end of the catheter body proximal of the proximal telescoping member. A puller cable is attached to the distal end of the sheath which is fixed to the distal end of the distal telescoping member for effecting radial expansion of the anchoring and stabilizing devices. In particular, proximal movement of the puller cable draws in the distal and proximal telescoping members for radially expanding the spines of the anchoring and stabilizing devices.

In either embodiment, the degree of radial expansion of both the anchoring and stabilizing devices is adjustable by adjusting the amount of relative translational movement between the sheath and the catheter body. The ability to adjust the degree of radial expansion of the anchoring and stabilizing devices enables the exertion of varying degrees of pressure on either the walls or the ostium of the tubular region. Accordingly, the anchoring and stabilizing devices are capable of conforming to differently shaped tubular regions. Also, in order to prevent undesired damage to the walls of the tubular region, the stabilizing device absorbs any excess pressure inadvertently exerted on the anchoring device. To that end, stops, for example in the form of rings fixedly mounted on the catheter body or the telescoping portion limit the amount of radial expansion of the anchoring device and/or the stabilizing device.

BRIEF DESCRIPTION OF THE DRAWINGS

These and other features and advantages of the present invention will be better understood by reference to the following detailed description when considered in conjunction with the accompanying drawings, wherein.

DETAILED DESCRIPTION

Figure 1:
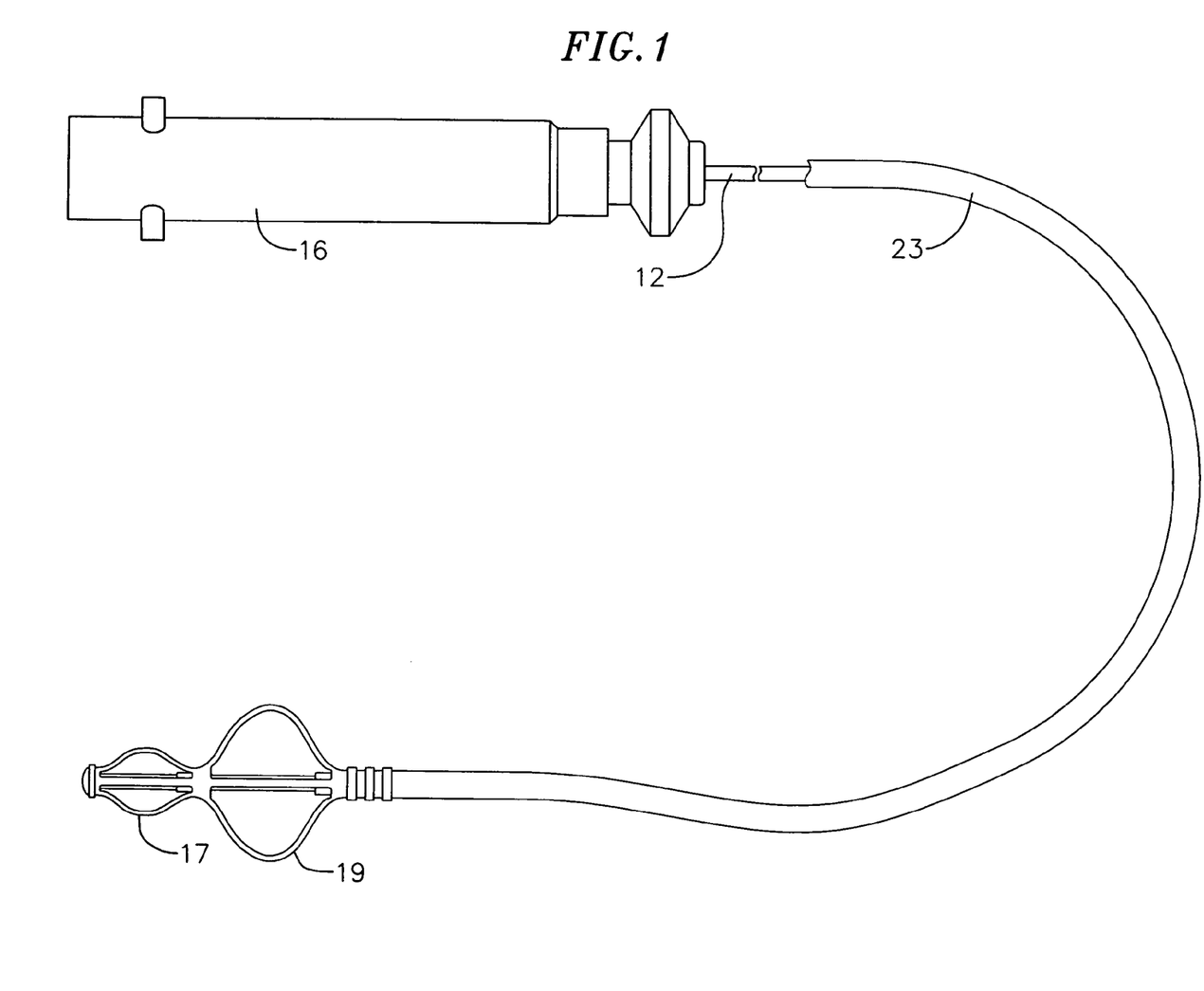
FIG. 1 is a perspective view of an embodiment of a catheter according to the present invention.

The invention is directed to a catheter 10 having anchoring and stabilizing devices located at or near the catheter's distal end. As shown in FIG. 1, the catheter comprises an elongated catheter body 12 having proximal and distal ends 13 and 15, a control handle 16 at the proximal end of the catheter body, and an anchoring device 17 located at the distal end of the catheter body 12. The catheter may optionally further comprise a stabilizing device 19 located at the distal end of the catheter body 12 proximal the anchoring device 17.

Figure 5:
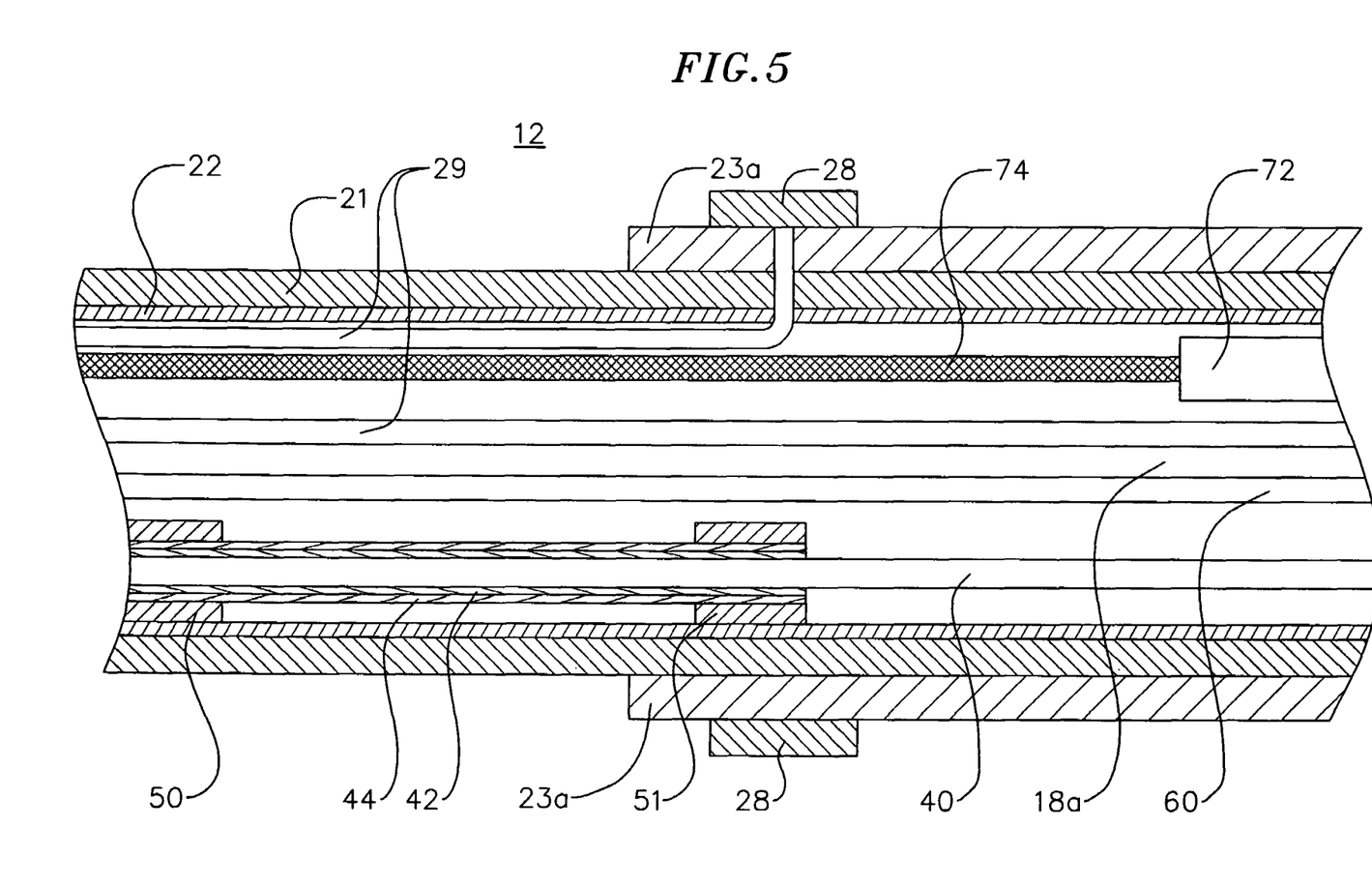
FIG. 5 is a longitudinal cross-sectional view of a portion of a catheter body of FIGS. 3 and 3A.
Figure 6:
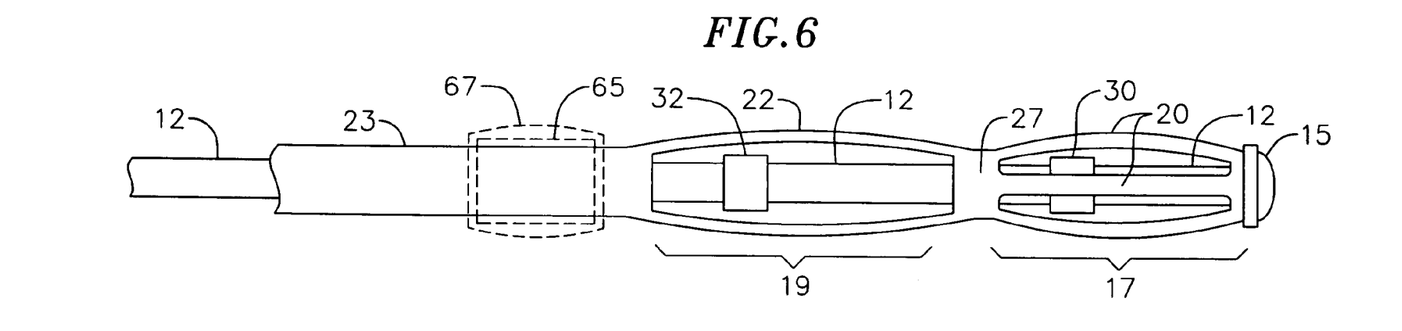
FIG. 6 is an enlarged perspective view of the distal end of the catheter body according to another embodiment of the invention
Figure 6A:
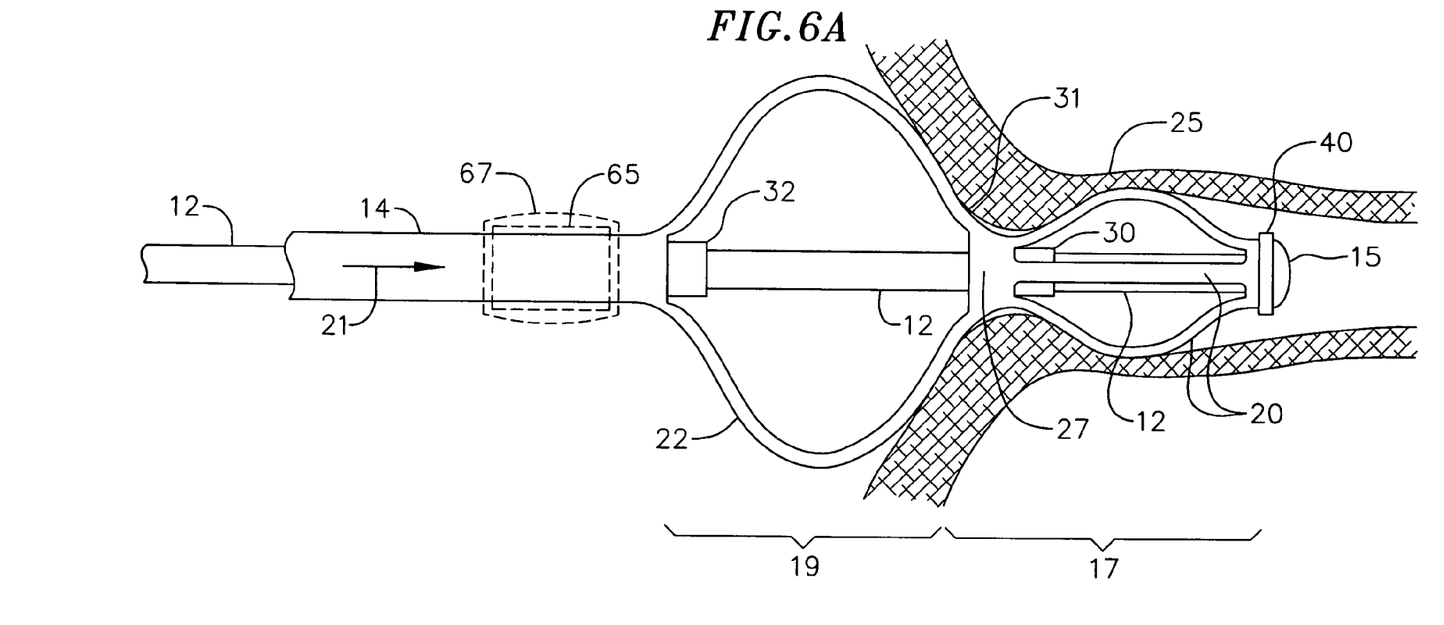
FIG. 6A is an enlarged perspective view of the catheter of FIG. 6, as deployed in a tubular region of a patient's heart.
Figure 7:
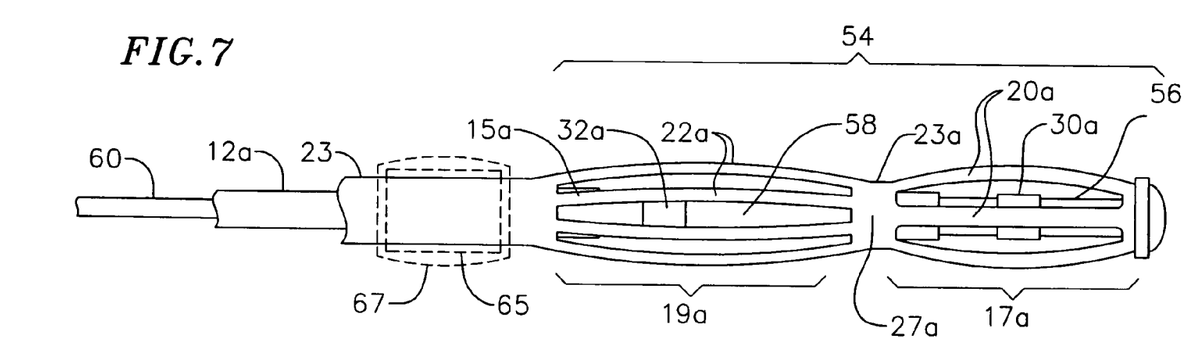
FIG. 7 is an enlarged perspective view of the distal end of the catheter body according to another embodiment of the invention.
Figure 7A:
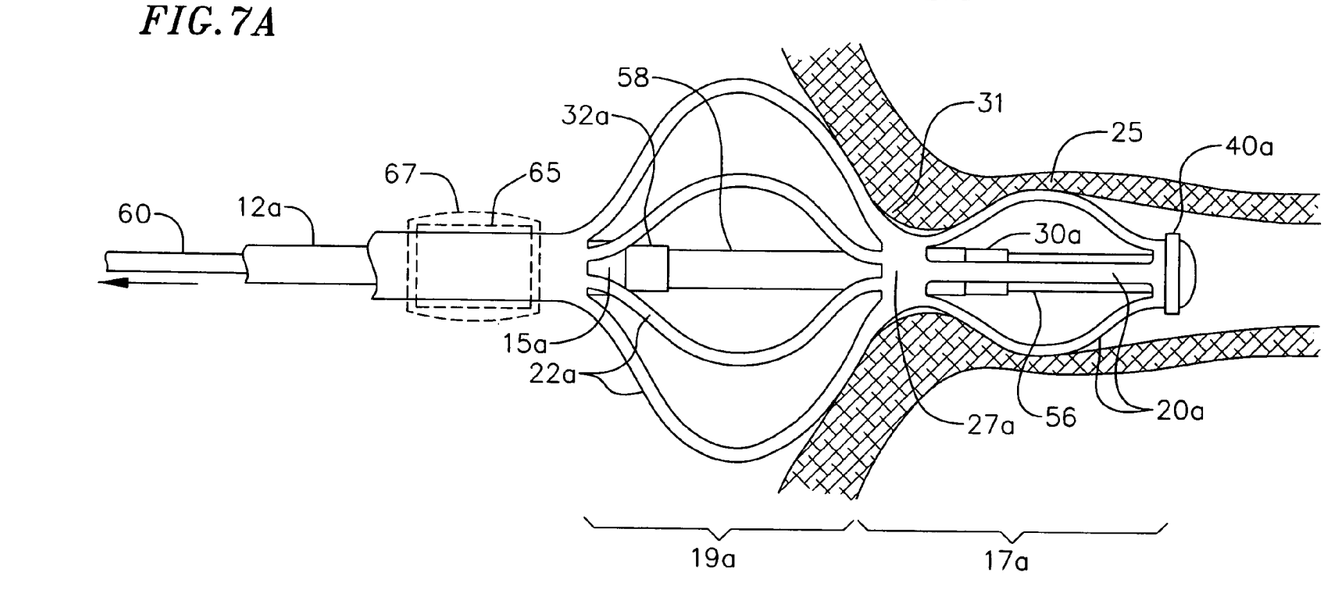
FIG. 7A is an enlarged perspective view of the catheter of FIG. 7, as deployed in a tubular region of a patient's heart.

As shown in FIG. 5, the catheter body 12 comprises an elongated tubular construction having a single, axial or central lumen 18, but can optionally have multiple lumens if desired. The catheter body 12 is flexible, i.e., bendable, but substantially non-compressible along its length. The catheter body 12 can be of any suitable construction and made of any suitable material. A presently preferred construction comprises an outer wall 21 made of polyurethane or PEBAX (polyether block amide). The outer wall 21 comprises an imbedded braided mesh of stainless steel or the like to increase torsional stiffness of the catheter body 12 so that, when the control handle 16 is rotated, the distal end of the catheter body 12 will rotate in a corresponding manner.

The outer diameter of the catheter body 12 is not critical, but is preferably no more than about 8 french, more preferably about 7 french. Likewise, the thickness of the outer wall 21 is not critical, but is preferably thin enough so that the central lumen 18 can accommodate a puller wire, lead wires, sensor cables and any other wires, cables or tubes. If desired, the inner surface of the outer wall 21 is lined with a stiffening tube 27 to provide improved torsional stability.

Figure 2:
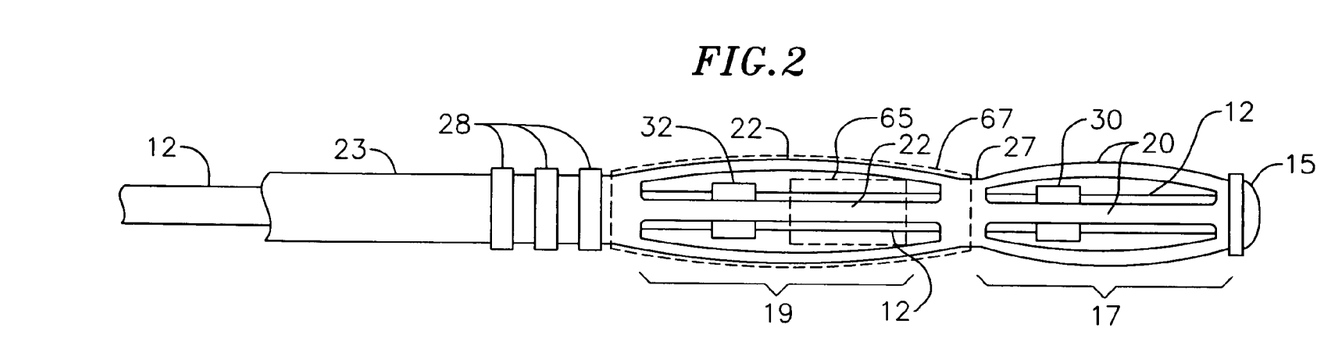
FIG. 2 is an enlarged perspective view of the distal end of the catheter body according to one embodiment of the invention
Figure 2A:
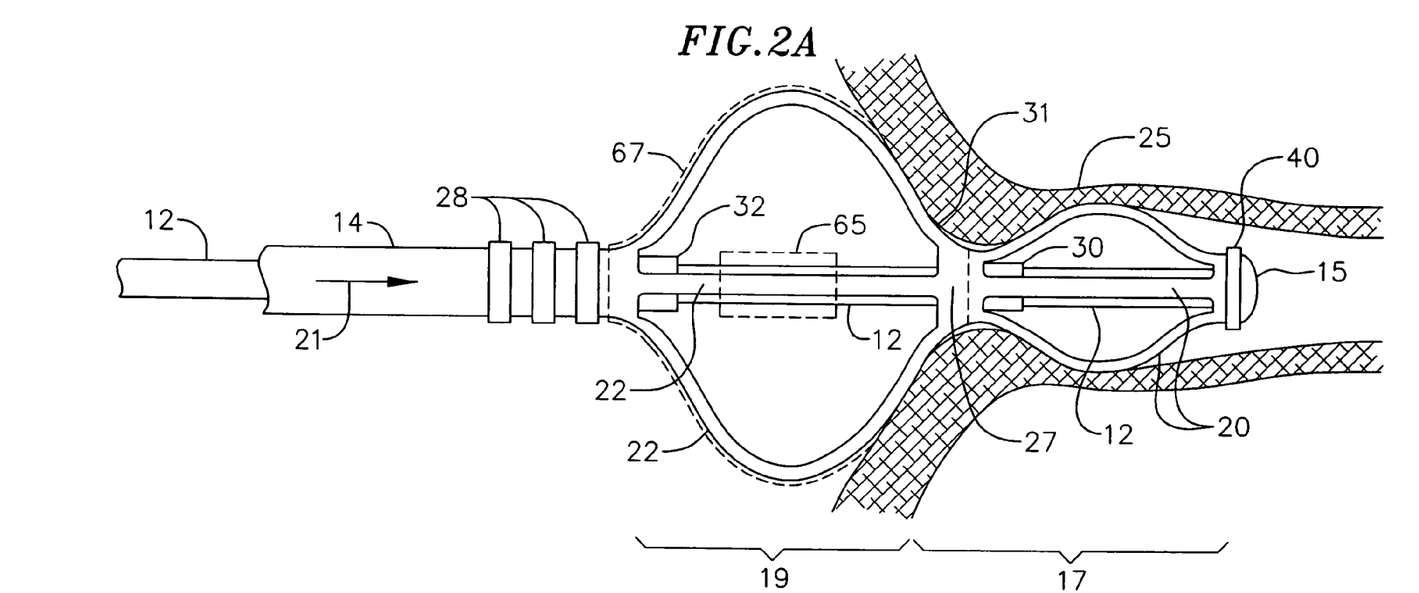
FIG. 2A is an enlarged perspective view of the catheter of FIG. 2, as deployed in a tubular region of a patient's heart.

The anchoring device 17 is located at the distal end of the catheter body 12. As shown in FIG. 2, the anchoring device 17 comprises at least two, and preferably at least four, spines 20 extending generally along a longitudinal axis of the catheter body, in radial symmetry about the catheter body. In the illustrated embodiment, the anchoring device 17 is formed by cutting slits in the circumference of a portion of a sheath 23 that generally extends the length of the catheter body and covers the catheter body 12 between the proximal and distal ends 13 and 15. In the embodiment of FIG. 2, a distal end of the sheath 23 is fixed to the distal end 15 of the catheter body 12 with the remainder of the sheath 23 proximal thereof being slidable relative to the catheter body 12. The slits in the sheath 23 form the spines 20 of the anchoring device 17. The spines 20 of the anchoring device 17 of the illustrated embodiment are generally equal in length and width and are sufficiently long such that upon compression of the anchoring device 17, the spines 20 expand radially to a degree sufficient to anchor the catheter within a tubular region 25, such as the pulmonary vein, against proximal and/or rotational movement (FIG. 2a). It is understood by one of ordinary skill in the art that the spines 20 may be formed with unequal lengths and/or unequal widths, if desired, to provide the anchoring device 17 with a nonsymmetrical radial expansion.

The stabilizing device 19 proximal the anchoring device 17 by a non-expanding section of the sheath 27 also comprises at least two, and preferably at least four, spines 22 extending generally along a longitudinal axis of the catheter body, in radial symmetry about the catheter body 12. The stabilizing device 19 is constructed substantially the same as the anchoring device 17. Slits are cut about the circumference of a portion of the sheath 23 covering the catheter body 12 proximal the anchoring device 17. These slits form the spines 22 of the stabilizing device 19. The spines 22 of the stabilizing device 19 of the illustrated embodiment are generally equal in length and width but are generally longer than the spines 20 of the anchoring device 17 such that the spines 22 bow outwardly to a radial expansion greater than that of the spines 20. As shown in FIG. 2a, the spines 21 bow out to a greater radial expansion such that the stabilizing device 19 can be flush against an ostium 31 of the pulmonary vein to stabilize the distal end of the catheter body against distal and/or rotational movement. It is understood by one of ordinary skill in the art that the slits may be formed with unequal lengths and/or unequal widths, if desired, to provide the stabilizing device with a nonsymmetrical radial expansion.

The sheath 23 is made of any flexible, nonconducting and noncompressible material such that upon distal movement compressing the sheath 23 toward the distal end 15 of the catheter body 12 the spines 20 of the anchoring device 17 bow outwardly to a desired degree of radial expansion, as shown in FIG. 2a. The sheath may be made of a polymer or polymer blend or any other biocompatible material for use in a patient's body. In the illustrated embodiment, the anchoring device 17 may be deployed by manually advancing the sheath 12a distally relative to the catheter body at or near the proximal end of the sheath that is outside of the patient's body, thereby advancing distally the remainder of the sheath in the patient's body which in turn compresses the anchoring device 17 at the distal end of the sheath, and radially expands the spines 20.

Preferably, the catheter body 12 comprises a stop for limiting the compression of the anchoring device. The catheter body may also comprise another stop for limiting the compression of the stabilizing device. The stops may take any suitable shape such that they limits the distal advancement of the sheath 23. For example, as shown in FIGS. 2 and 2a, the stops may comprise rings 30 and 32 fixedly positioned at predetermined locations on the catheter body 12. In particular, the ring 30 is positioned at a location between the distal end 15 of the catheter body and a proximal end of the anchoring device 17 and the ring 32 is positioned between a proximal end and a distal end of the stabilizing device 19. When the proximal end of the anchoring device 17 reaches the ring 30 the anchoring device cannot compress further and is at a radial maximum; likewise, when the proximal end of the stabilizing device 19 reaches the ring 32 the stabilizing device 19 cannot compress further and is at a radial maximum. As such, radial expansion of the anchoring device 17 and/or the stabilizing device 19 is limited in accordance with the fixed positioning of the rings 30 and 32, respectively, on the catheter body 12.

Longitudinal movement of the sheath 23 is accomplished, for example, by manual distal advancement by the user, or by suitable manipulation of the control handle 16. If desired, the control handle 16 may include a stopping mechanism for locking the sheath 23 in place relative to the catheter body upon reaching the desired degree of radial expansion of the anchoring device 17 and/or the stabilizing device 19, the stopping mechanism of the control handle working independently from the stop or the ring 30 of the anchoring device 17. The stopping mechanism of the control handle may take any suitable shape such that the sheath 23 is locked in place, preventing any further distal and/or proximal movement of the sheath 12a. For example, a clamp ring 34 may be provided on a proximal end of the sheath which is adapted to releasably clamp sheath to the catheter body to prevent distal and/or proximal movement of the proximal end of the sheath.

In accordance with the present invention, distal advancement of the sheath 23 relative to the catheter body 12 results in compression of the stabilizing device 19 and/or the anchoring device 17, with generally but not necessarily compression of the anchoring device 17 occurring before compression of the stabilizing device 19. In use, the catheter is advanced in its atraumatic configuration (see FIG. 2) in the patient's body until it reaches the heart chamber. There, the distal end of the catheter body is placed inside the tubular region 25, e.g., the pulmonary vein, and the sheath 23 is advanced distally such that the anchoring device 17 is radially expanded to an appropriate level or until the proximal end of the anchoring device encounters the ring 30. The stabilizing device 19 is also radially expanded by distal advancement of the sheath to an appropriate level or until the proximal end of the stabilizing device encounters the ring 32. Accordingly, as shown in FIG. 2A, the radial expansion of the anchoring device secures the anchoring device to the inside of the pulmonary vein against rotational and/or proximal movement while the radial expansion of the stabilizing device presses the stabilizing device against the ostium 31 to prevent or at least minimize rotational and/or distal movement. With the distal end 15 of the catheter body 12 secured in this manner to the tubular region 25, the catheter is ready for ablation by means of a distal electrode 40 and/or an ultrasonic ablation member 42, as described in detail further below.

In accordance with the present invention, when the anchoring device 17 reaches its maximum degree of radial expansion, the stabilizing device 19 absorbs any excess pressure exerted by the continued advancement of the sheath 23. This construction prevents the anchoring device 17 from absorbing any excess pressure, thereby preventing the anchoring device 17 from causing any undue damage to the walls of the tubular region. Alternatively, the stop, such as the rings 30 and 32, may be used to prevent the anchoring device 17 and/or stabilizing device 19 from absorbing any excess pressure. The stopping mechanism, e.g., the clamp ring 34 may also be used to lock the stabilizing device 19 in radial expansion to press on the ostium of the pulmonary vein.

When the distal end 15 of the catheter body 12 needs to be withdrawn from the tubular region 25, the clamp ring 34 is released and the sheath 23 is moved manually by the user in the proximal direction to minimize and reduce the radial expansion of the anchoring device 17 and the stabilizing device 19. Having returned to its atraumatic configuration, the distal end 15 can be readily removed from the tubular region and reposition in another tubular region or removed altogether from the patient's body.

Figure 4:
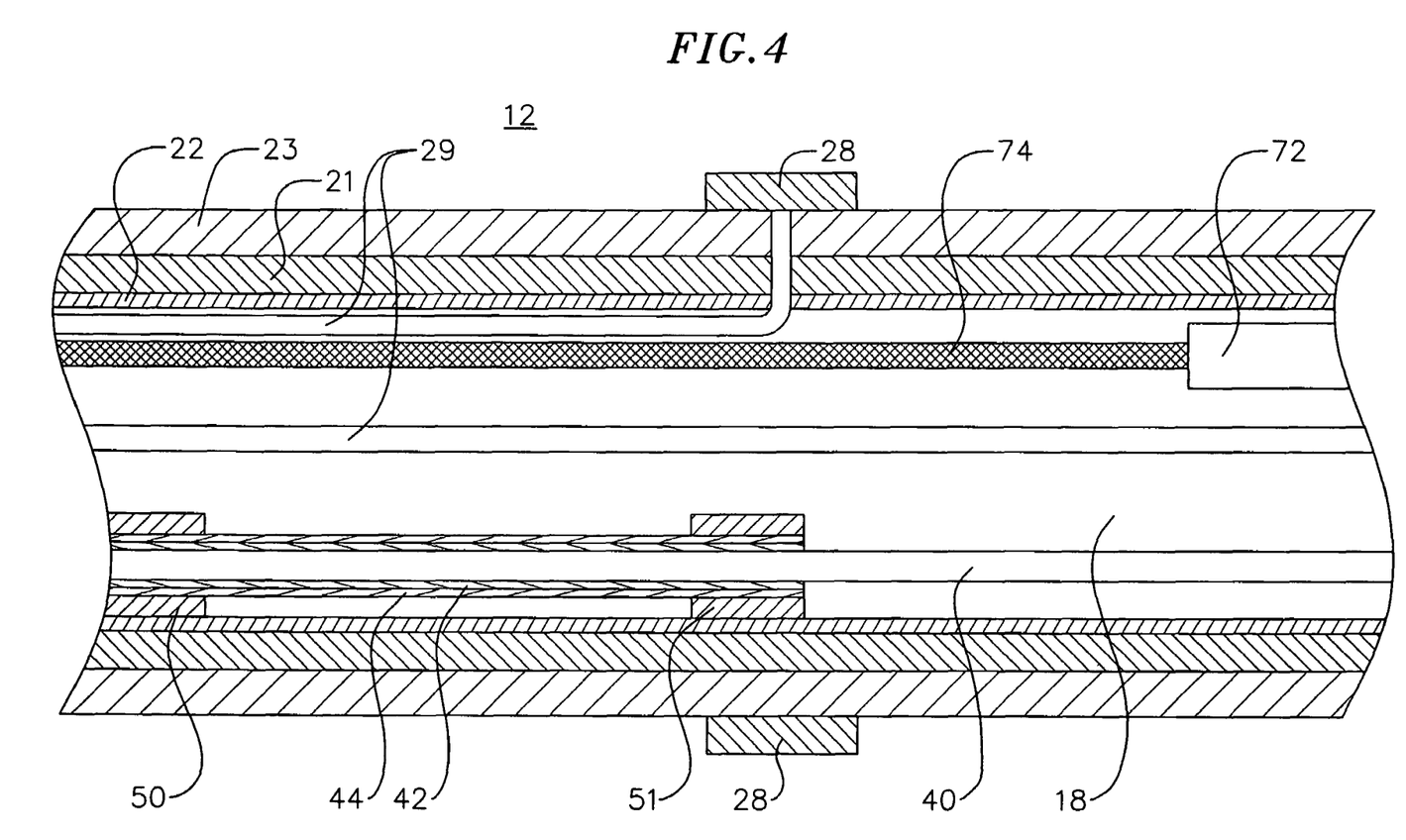
FIG. 4 is a longitudinal cross-sectional view of a portion of a catheter body of FIGS. 2 and 2A.

In an alternative embodiment, shown in FIG. 4, a sheath 23a covers a distal end 15a of a catheter body 12a which is adapted with a telescoping portion 54 having two telescoping members 56 and 58. In the illustrated embodiment, a sheath 23a has a shortened length, extending from a distal end of the telescoping portion 54 to only proximally past a proximal end of the telescoping portion 54. A distal end of the sheath 23a is fixed to the distal end of the telescoping portion and a proximal end of the sheath is fixed to the distal end of the catheter body 15. An anchoring device 17a formed from a distal portion of the sheath 23a is located generally on the telescoping member 54 and a stabilizing device 19a formed from a proximal portion of the sheath is located on the telescoping member 56. A non-expanding section 27a of the sheath separates the devices 17a and 19a. As described above, slits are cut around the circumference of the sheath 23a, forming spines 20a and 22a of the anchoring device 17a and the stabilizing device 19a, which can be generally equal or generally unequal in length and width. The stabilizing device 19a proximal the anchoring device 17a is longer than the anchoring device 17a, but is sufficiently short to allow room on the distal end of the catheter body 12 for an ablation device to be mounted proximal the stabilizing device 19a, such as ring electrodes discussed in detail further below.

For deploying the anchoring device 17a and/or the stabilizing device 19a into their radially expanded configuration, a noncompressible and generally stiff puller cable 60 extends through a lumen in the telescoping portion and the lumen 18a of the catheter body 12a and is fixed at its distal end to the distal end of the telescoping portion 54 which in turn is fixed to the distal end of the sheath 23a. A proximal end of the puller cable 60 is located in the control handle 16 and connected to suitable control mechanism that moves the puller cable 60 proximally and distally. Proximal movement of the puller cable 60 results in compression of the anchoring device 17a and/or the stabilizing device 19a. This compression causes the spines 20a and 22a to bow outwardly, thereby causing the anchoring device and the stabilizing device to expand radially. The curvature of the spines 20a and 22a, and thus the degree of radial expansion of the anchoring device 17a and the stabilizing device 19a, can be adjusted by controlling the proximal distance in which the puller cable 60 is pulled. The telescoping member 56 may include a stop, such as a ring 30a, for preventing further radial expansion of the anchoring device 17a after reaching a predetermined degree of radial expansion. Likewise, the telescoping member 58 may include a stop, such as a ring 32a, for preventing further radial expansion of the stabilizing device 19a after reaching a predetermined degree of radial expansion. The rings 30a and 32a are fixedly positioned on the respective telescoping members 56 and 58 such that when the ring 32a encounters the distal end of the catheter body 12, the telescoping member 58 is prevented from further proximal movement, and/or when the ring 30a encounters a distal end of the telescoping member 58 the telescoping member 56 is prevented from further proximal movement.

Figure 3:
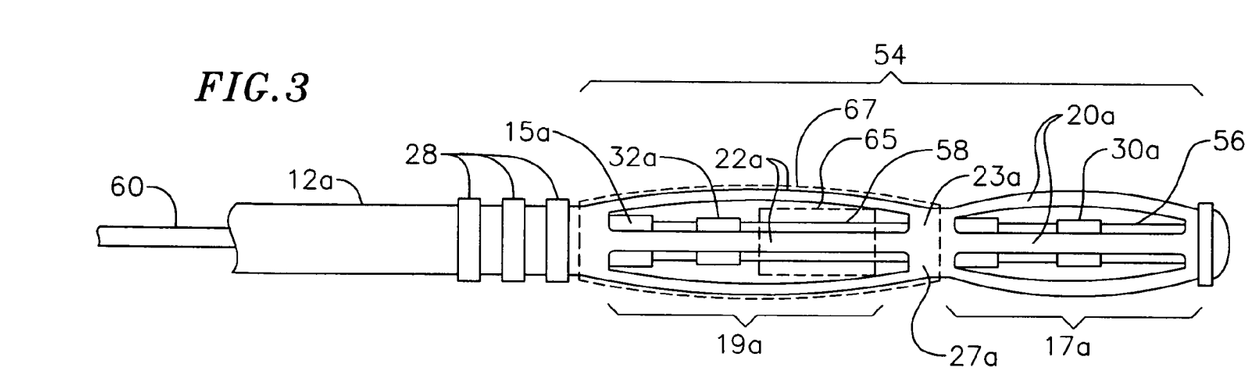
FIG. 3 is an enlarged perspective view of the distal end of the catheter body according to another embodiment of the invention.
Figure 3A:
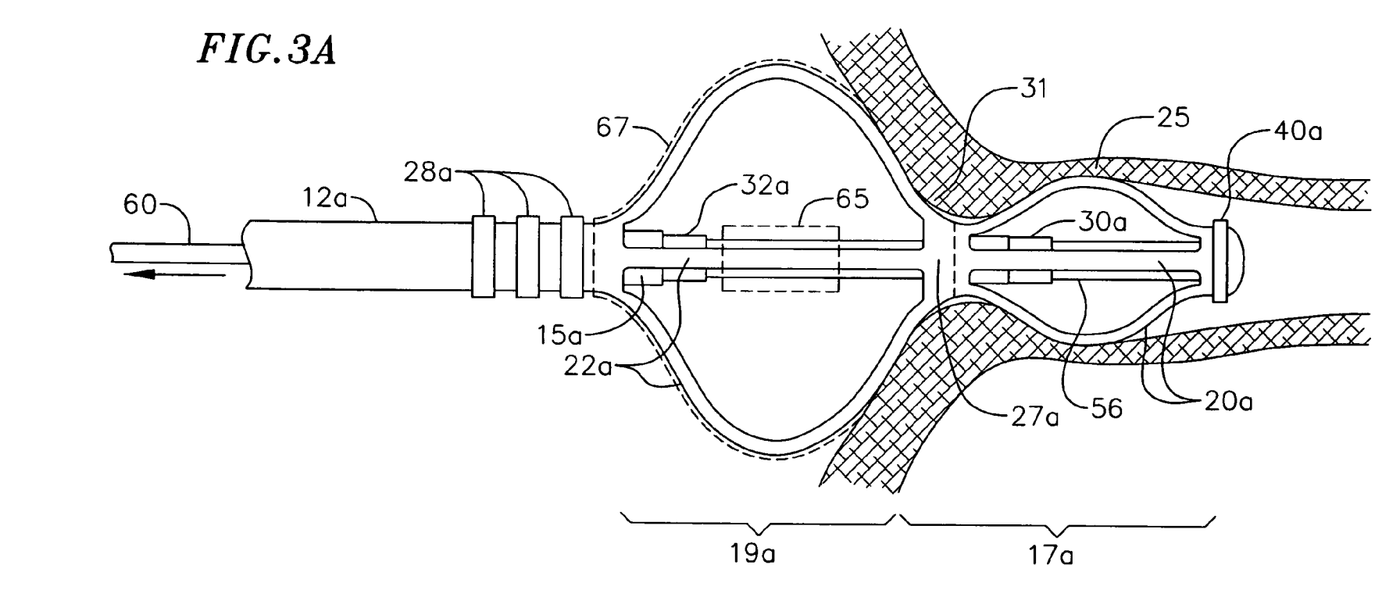
FIG. 3A is an enlarged perspective view of the catheter of FIG. 3, as deployed in a tubular region of a patient's heart.

In accordance with the present invention, proximal movement of the puller cable 60 drawing in the distal end of the telescoping member 56 results in compression of the stabilizing device 19a and/or the anchoring device 17a, with generally but not necessarily compression of the stabilizing device 19a occurring before compression of the anchoring device 17a. In use, the catheter is advanced in its atraumatic configuration (see FIG. 3) in the patient's body until it reaches the heart chamber. There, the distal end of the telescoping member 56 is placed inside the tubular region 25, e.g., the pulmonary vein, and the puller cable 60 is drawn proximally by suitable manipulation of the control handle 16 which in turn draws proximally the telescoping members 56 and 58. As shown in FIG. 3A, the stabilizing device 19a is radially expanded to an appropriate level or until the ring 32a encounters the distal end 15 of the catheter body 12 and the anchoring device 17a is radially expanded to an appropriate level or until the ring 30a encounters the proximal end of the telescoping member 58. Accordingly, the radial expansion of the anchoring device 17a secures the anchoring device to the inside of the tubular region 25, e.g., a pulmonary vein, against rotational and/or proximal movement while the radial expansion of the stabilizing device 19a presses the stabilizing device against the ostium 31 of the tubular region to prevent or at least minimize rotational and/or distal movement. With the distal end of its catheter body secured in this manner, the catheter is ready for ablation by means of a distal electrode 40a and/or an ultrasonic ablation member 42a, as described in detail further below.

When the anchoring device 17a reaches its maximum degree of radial expansion, the stabilizing device 19a absorbs any excess pressure exerted by the continued advancement of the sheath 23a. This construction prevents the anchoring device 17a from absorbing any excess pressure, thereby preventing the anchoring device 17a from causing any undue damage to the walls of the tubular region. Alternatively, the stops, such as the rings 30a and 32a, may be used to prevent the anchoring device 17a and/or stabilizing device 19a from absorbing any excess pressure. The mechanism controlling the puller cable 60 may also be adapted to lock the cable in place to prevent distal and/or proximal movement after the devices 17a and 19a have been deployed at or near the ostium of the pulmonary vein.

Accordingly, the puller cable 60 attached to the distal end of the sheath 23a controls the radial expansion of both the anchoring device 17a and the stabilizing device 19a. Proximal movement of the puller cable 60 results in compression of both the anchoring device 17a and the stabilizing device 19a. This compression causes the spines 20a and 22a to bow outwardly, thereby causing the anchoring device 17a and the stabilizing device 19 to expand radially. The curvature of the spines 20 and 20a, and thus the degree of radial expansion of the anchoring device 17 and the stabilizing device 19, can be adjusted by controlling the proximal distance by which the puller cable 60 is pulled.

When the telescoping portion 54 needs to be withdrawn from the tubular region 25, the control handle 16 is manipulated to advance the puller wire 60 so as to minimize and reduce the radial expansion of the anchoring device 17 and the stabilizing device 19. It is understood by one of ordinary skill in the art that the puller cable 60 has sufficient stiffness and/or is appropriately supported by its own sheath such that it can adequately support and maintain the telescoping portion 54 in its distally extended configuration from the distal end of the catheter body when the catheter body is being advanced in the patient's body and also adequately extend the telescoping members 56 and 58 to return the distal end to its atraumatic configuration. Having returned to its atraumatic configuration, the catheter body 12 can be readily removed from the tubular region and repositioned in another tubular region or removed altogether from the patient's body.

It is understood by one of ordinary skill in the art that the telescoping portion 54 may also consist of merely one telescoping member or more than two telescoping members, as desired or appropriate to vary the compression of the anchoring device and/or the stabilizing device. Moreover, the ring 30 may be positioned on the telescoping 54 proximal of the section 27a, as desired or appropriate to limit the compression of the stabilizing device. The maximum distal extension of the telescoping portion regardless of the plurality of telescoping member(s) is limited by the length of the puller cable 60 and/or the provision of a lip or flange at the corresponding ends of adjacent telescoping members which prevents the telescoping members from disconnecting.

In any of the above embodiments, the radial expansion of the anchoring device and the stabilizing device is adjustable. The ability to adjust the radial expansion of the anchoring device enables the exertion of varying degrees of pressure on the walls of the tubular region, e.g. the pulmonary vein. For example, a physician can manipulate the catheter to expand the devices until enough pressure is exerted on the walls of the tubular region to anchor the catheter within that region, and then activate the stopping mechanism to lock the devices in their position. Once locked, no more, or no less, pressure can be exerted on the walls of the tubular region and/or the ostium. The ability to adjust the radial expansion of the anchoring device enables the devices to conform to many different shapes within any tubular region or ostium. This ability, therefore, is extremely advantageous, since the shapes and contours of tubular regions and ostiums vary within the heart and vary in different patients. In addition, the ability to control the pressure exerted on the walls of the tubular region and the ostium enables the anchoring and stabilizing of the catheter against both translational and rotational movement. Because the stabilizing device is located proximal the anchoring device, the stabilizing device is capable of absorbing any excess pressure that may inadvertently be exerted on the anchoring device. Such a construction prevents the anchoring device from causing any undue or excessive damage to the walls of the tubular region.

Figure 8:
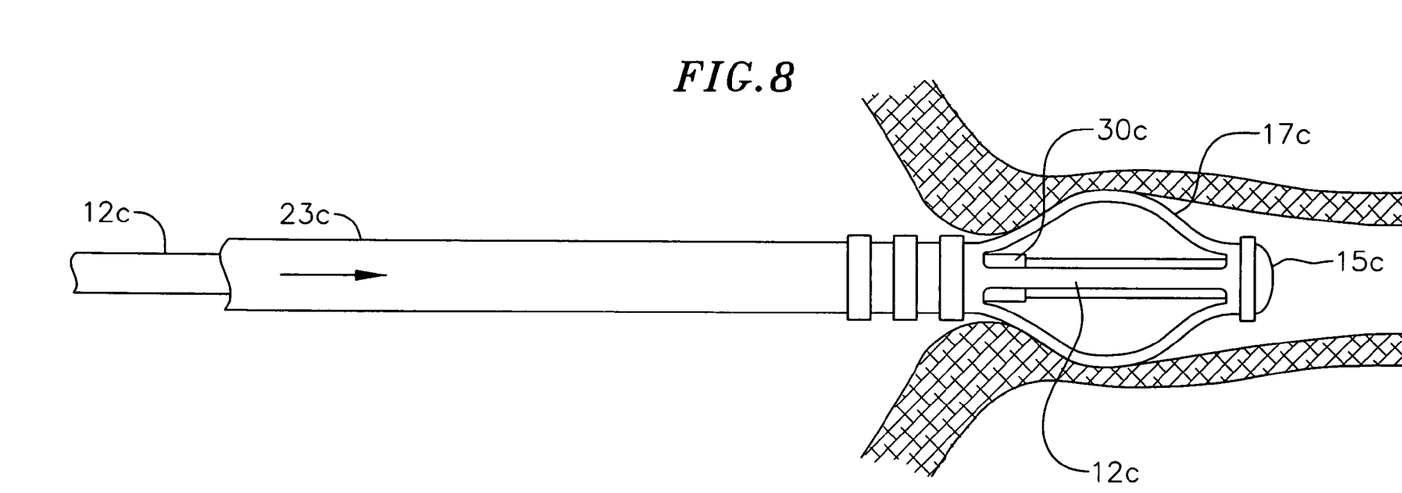
FIG. 8 is a perspective view of another embodiment of a catheter of the present invention without a stabilizing device.
Figure 9:
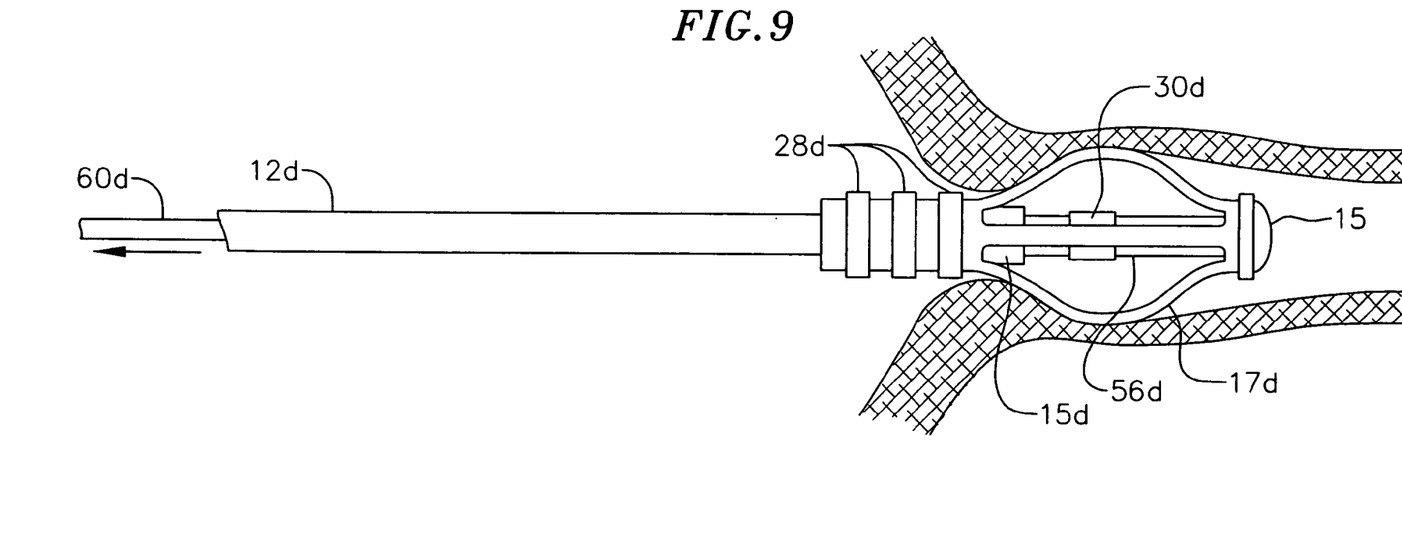
FIG. 9 is a perspective view of yet another embodiment of a catheter of the present invention without a stabilizing device.

As shown in FIG. 8, a catheter body 12c may be configured with merely an anchoring device 17c formed from a sheath 23c whose distal end is fixed to a distal end 15c of the catheter body. A maximum radial expansion of the device 17c is set by a ring 30c fixedly positioned on the catheter body 12c. Moreover, as shown in FIG. 9, a catheter body 12d may be configured with merely an anchoring device 17d formed from a sheath 23d whose distal end is fixed to a distal end of a telescoping member 56d that is moved distally and proximally by a puller cable 60d. A maximum radial expansion of the device 17d is set by a ring 30d fixedly positioned on the member 56d. For either of these embodiments, an ultrasonic transducer and protective balloon may be mounted proximal of the anchoring device, if desired.

One or more ring electrodes may optionally be mounted on the sheath of either catheter embodiment. In particular, as shown in FIGS. 2, 2a, 3 and 3a, ring electrodes 28 are preferably mounted on the sheath distal the anchoring device and proximal the stabilizing device. The ring electrodes 28 may be used for mapping and/or ablation. Accordingly, each of the ring electrodes 28 is electrically connected to an appropriate mapping or monitoring system and/or source of ablation energy by means of an electrode lead wire 29, as shown in FIGS. 4 and 5. Each electrode lead wire 29 extends through the control handle 16 and 16a, through a lumen in the catheter body 12 and 12a, and is connected to its corresponding ring electrode 28 (of which only one is shown in FIGS. 4 and 5). Each lead wire 29 is covered by a non-conductive covering and is attached to its corresponding ring electrode 28 by any suitable method.

A preferred method for attaching a lead wire 29 to a ring electrode 28 involves first making a small hole through the wall of the sheath 23 and 23a. Such a hole can be created, for example, by inserting a needle through the sheath and heating the needle sufficiently to form a permanent hole. The lead wire 29 is then drawn through the hole by using a microhook or the like. The end of the lead wire 29 is then stripped of any coating and welded to the underside of the ring electrode 28, which is then slid into position over the hole and fixed in place with polyurethane glue or the like. Alternatively, each ring electrode 28 is formed by wrapping a lead wire 29 around the sheath 23 and 23a a number of times and stripping the lead wire 29 of its own insulated coating on its outwardly facing surfaces.

In the catheter 12 of FIGS. 2, 2a and 4, each lead wire 29 is significantly longer than the length between the ring electrode and the connection of the lead wire 29 to the control handle. This extra length of the lead wires 29 allows the lead wires 29 to move with the sheath 23 distally to radially expand the spines 20 of the anchoring device 17 and/or the spines 22 of the stabilizing device 19. When the sheath is so moved, the lead wires 29 pass between the sheath 23 and the catheter body 12. As would be recognized by one skilled in the art, the extra length of the lead wires 29 may be contained in the control handle 16 by a mechanism capable of deploying the extra length as needed.

Alternatively, as shown in FIGS. 2, 2A, 3 and 3A, the catheter body may carry a circumferential ablation device, such as an ultrasound transducer 65 mounted within the stabilization device 19 and 19a. In such an arrangement, the stabilization device is covered with an expandable balloon 67 whose distal and proximal ends are fixed to the sheath 23 and 23a to seal the ultrasound transducer 65 from blood and other fluids present in the heart and the tubular region. An example of such an ultrasound transducer and balloon mechanism suitable for use in the present invention is disclosed in U.S. Pat. No. 6,780,183, the disclosure of which is incorporated herein by reference. Because the ultrasound transducer 65 cannot transmit ablation energy through the spines of the stabilizing device, a suitable embodiment of the stabilizing device 19 preferably comprises at least two, but no more than three spines. Such a configuration allows the ultrasound transducer 65 to transmit ablation energy to the target site, but still stabilizes the catheter, e.g., about the ostium of the pulmonary vein.

In an alternative embodiment, as shown in FIGS. 6, 6A, 7 and 7A, the ultrasound transducer 65 is mounted on the sheath 23 and 23a proximal the stabilizing device 19 and 19a and is covered by an inflatable balloon 67 fixedly attached at its proximal and distal ends to the sheath. In this embodiment, the stabilizing device 19 and 19a preferably comprises at least two, but no more than 3 spines, to enable the transducer 31 to transmit ablation energy around the stabilizing device 19.

For any of the foregoing embodiments, the catheter optionally further comprises a means for deflecting the distal end of the catheter body 12 and 12a. The deflection means comprises a puller wire 40 anchored at its distal end to the distal end of the catheter body, as shown in FIGS. 4 and 5. The puller wire 40 is made of any suitable metal, such as stainless steel or Nitinol, and is preferably coated with Teflon or the like. The coating imparts lubricity to the puller wire 40. The puller wire preferably has a diameter ranging from about 0.006 to about 0.010 inches.

A compression coil 42 is situated within the catheter body in surrounding relation to the puller wire 40. The compression coil extends from the proximal end of the catheter to the distal end of the catheter. The compression coil 42 is made of any suitable metal, preferably stainless steel. The compression coil 42 is tightly wound on itself to provide flexibility, i.e., bending, but to resist compression. The inner diameter of the compression coil 42 is preferably slightly larger than the diameter of the puller wire 40. For example, when the puller wire 40 has a diameter of about 0.007 inches, the compression coil 42 preferably has an inner diameter of about 0.008 inches. The Teflon coating on the puller wire 40 allows it to slide freely within the compression coil 42. Along its length, the outer surface of the compression coil 42 is covered by a flexible, non-conductive sheath 44 to prevent contact between the compression coil 42 and the lead wires 29 within the catheter body 12. A non-conductive sheath 44 made of polyimide is presently preferred.

The compression coil 42 is anchored at its proximal end to the proximal end of the stiffening tube 22 of the catheter body 12 by glue joint 50 and at its distal end to the distal end of the catheter body 12 by glue joint 51. Both glue joints 50 and 51 preferably comprise polyurethane glue or the like. The glue may be applied by means of a syringe or the like through a hole made between the outer surface of the catheter body 12 and the single lumen 18. Such a hole may be formed, for example, by a needle or the like that punctures the wall of the catheter body 12 and the stiffening tube 22 which is heated sufficiently to make a permanent hole. The glue is then introduced through the hole to the outer surface of the compression coil 42 and wicks around the outer circumference to form a glue joint about the entire circumference of the compression coil 42.

The puller wire 40 extends through the lumen of the catheter body 12 into the distal end of the catheter body 12. The distal end of the puller wire 40 is anchored within the distal end of the catheter body 12. The puller wire 40 extends through a plastic, preferably Teflon, sheath 45, which prevents the puller wire 40 from cutting into the wall of the catheter body 12 when the distal end of the catheter body 12 is deflected. The puller wire 40 is deflected upon longitudinal movement of the puller wire 40 relative to the catheter body 12.

An electromagnetic sensor 72 may be contained within the distal end of the catheter body 12. The electromagnetic sensor 72 may extend from the distal end of the catheter body 12 to the distal end of the anchoring device 17. Alternatively, the electromagnetic sensor 72 may extend partially into the anchoring device 17. The electromagnetic sensor 72 is mounted to the distal end of the catheter body 12 by any suitable means, e.g. by polyurethane glue or the like.

The electromagnetic sensor 72 is connected to an electromagnetic sensor cable 74, which extends through the lumen in the catheter body 12, and out through the control handle 16. The electromagnetic sensor cable 74 comprises multiple wires encased within a plastic covered sheath. In the control handle 16, the sensor cable 74 is connected to a circuit board (not shown). The circuit board amplifies the signal received from the electromagnetic sensor 72 and transmits it to a computer in a form understandable by the computer. Because the catheter is designed for a single use only, the circuit board may contain an EPROM chip which shuts down the circuit board approximately 24 hours after the catheter has been used. This prevents the catheter, or at least the electromagnetic sensor from being used twice.

Suitable electromagnetic sensors for use with the present invention are described, for example, in U.S. Pat. Nos. 5,558,091, 5,443,489, 5,480,422, 5,546,951, and 5,391,199, the disclosures of which are incorporated herein by reference. A preferred electromagnetic sensor 72 has a length of from about 6 mm to about 7 mm and a diameter of about 1.3 mm.

Suitable control handle mechanisms for operating the puller cable 60 and/or the puller wire 40 may be found in U.S. Pat. Nos. 6,210,407, 6,171,277 and 6,198,974, the disclosures of which are incorporated herein by reference.

The preceding description has been presented with reference to the presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support for the following claims which are to have their fullest and fairest scope.

What is claimed is:

1. A catheter adapted for use at or in a tubular region of the heart, comprising:
    an elongated catheter body having proximal and distal ends;
    an expandable and retractable anchoring device adapted to limit rotational and proximal movement of the distal end of the catheter body relative to the tubular region when said anchoring device is radially expanded, wherein the anchoring device is adapted to sit inside the tubular region and to press against an inner circumferential wall of the tubular region when radially expanded;
    an expandable and retractable stabilizing device proximal of the anchoring device and adapted to limit rotational and distal movement of the distal end of the catheter body relative to the tubular region when said stabilizing device is radially expanded, wherein the stabilizing device is adapted to sit at or near an ostium of the tubular region and to press against the ostium when radially expanded;
    wherein the anchoring device and the stabilizing device are formed from slits cut in a sheath positioned on at least the distal end of the catheter body and adapted for distal and proximal movement relative to the catheter body to radially expand the devices; and
    wherein at least one of the anchoring device and stabilizing device is positioned on a telescoping portion distal of the distal end of the catheter body and the telescoping portion is moved proximally to radially expand at least one of the anchoring and stabilizing devices.

2. A catheter according to claim 1, wherein the slits form spines extending in a longitudinal direction defined by the catheter body.

3. A catheter according to claim 2, wherein each spine of the anchoring device has the same length.

4. A catheter according to claim 2, wherein each spine of the stabilizing device has the same length.

5. A catheter according to claim 2, wherein the spines of the anchoring device differ in length from the spines of the stabilizing device.

6. A catheter of claim 1, wherein the sheath is moved distally to radially expand at least one of the devices.

7. A catheter of claim 1, wherein the sheath is moved proximally to radially expand at least one of the anchoring and stabilizing devices.

8. A catheter of claim 1, wherein the anchoring device is fixed to the distal end of the catheter body and the sheath is moved distally to radially expand at least one of the devices.

9. A catheter of claim 1, further comprising means for ablating tissue at or near the tubular region.

10. A catheter of claim 1, further comprising an electromagnetic sensor mounted in the distal end of the catheter body.

11. A catheter of claim 1, further comprising a circumferential ablation device mounted within the stabilizing device.

12. A catheter of claim 11, wherein the circumferential ablation device is an ultrasound transducer, and further wherein the stabilizing device is covered by an expandable balloon.

13. A catheter according to claim 1, further comprising an ablation device mounted on the sheath proximal the stabilizing device.

14. A catheter according to claim 13, wherein the ablation device is an ultrasound transducer encased within an expandable balloon.

15. A catheter according to claim 1, wherein the anchoring device has at least 4 spines.

16. A catheter according to claim 1, wherein the stabilizing device has at least 4 spines.

17. A catheter adapted for use at or in a tubular region of the heart, comprising:
    an elongated catheter body having proximal and distal ends;
    an expandable and retractable anchoring device adapted to limit rotational and proximal movement of the distal end of the catheter body relative to the tubular region when said anchoring device is radially expanded, wherein the anchoring device is adapted to sit inside the tubular region and to press against an inner circumferential wall of the tubular region when radially expanded;
    an expandable and retractable stabilizing device proximal of the anchoring device and adapted to limit rotational and distal movement of the distal end of the catheter body relative to the tubular region when said stabilizing device is radially expanded, wherein the stabilizing device is adapted to sit at or near an ostium of the tubular region and to press against the ostium when radially expanded;
    means for deflecting the distal end of the catheter body comprising a puller wire having a proximal end and a distal end, the proximal end of the puller wire being fixedly attached in a control handle at the proximal end of the catheter body, and the distal end of the puller wire is fixedly attached to the distal end of the catheter body, whereby longitudinal movement of the puller wire results in deflection of the distal end of the catheter; and
    wherein the anchoring device and the stabilizing device are formed from slits cut in a sheath positioned on at least the distal end of the catheter body and adapted for distal and proximal movement relative to the catheter body to radially expand the devices.

18. A catheter adapted for use at or in a tubular region of the heart, comprising:
    an elongated catheter body having proximal and distal ends;
    an expandable and retractable anchoring device adapted to limit rotational and proximal movement of the distal end of the catheter body relative to the tubular region when said anchoring device is radially expanded, wherein the anchoring device is adapted to sit inside the tubular region and to press against an inner circumferential wall of the tubular region when radially expanded;

an expandable and retractable stabilizing device proximal of the anchoring device and adapted to limit rotational and distal movement of the distal end of the catheter body relative to the tubular region when said stabilizing device is radially expanded, wherein the stabilizing device is adapted to sit at or near an ostium of the tubular region and to press against the ostium when radially expanded, wherein the anchoring device and the stabilizing device are formed from slits cut in a sheath positioned on at least the distal end of the catheter body and adapted for distal and proximal movement relative to the catheter body to radially expand the devices; and at least one ring electrode mounted on the sheath.

19. A catheter according to claim 18, wherein the at least one ring electrode is mounted on the sheath proximal the anchoring device.

20. A catheter of claim 18, wherein the at least one ring electrode is mounted on the sheath proximal the stabilizing device.

21. A catheter of claim 18, wherein the at least one ring electrode is mounted on the sheath distal the anchoring device.

22. A catheter adapted for use at or in a tubular region of the heart, comprising:
an elongated catheter body having proximal and distal ends;
an expandable and retractable anchoring device adapted to limit rotational and proximal movement of the distal end of the catheter body relative to the tubular region when said anchoring device is radially expanded, wherein the anchoring device is adapted to sit inside the tubular region and to press against an inner circumferential wall of the tubular region when radially expanded;
an expandable and retractable stabilizing device proximal of the anchoring device and adapted to limit rotational and distal movement of the distal end of the catheter body relative to the tubular region when said stabilizing device is radially expanded, wherein the stabilizing device is adapted to sit at or near an ostium of the tubular region and to press against the ostium when radially expanded, wherein the anchoring device and the stabilizing device are formed from slits cut in a sheath positioned on at least the distal end of the catheter body and adapted for distal and proximal movement relative to the catheter body to radially expand the devices; and
a stop limiting the radial expansion of at least one of the anchoring and stabilizing devices.

23. A catheter comprising:
an elongated catheter body having proximal and distal ends and at least one lumen extending therethrough;
a non-conductive sheath mounted in surrounding relation to the catheter body, wherein the non-conductive sheath is fixedly attached to the catheter body except at a distal end of the non-conductive sheath;
an anchoring device comprising a plurality of spines formed by cutting longitudinal slits about a circumference of the distal end of the non-conductive sheath;
a puller cable having proximal and distal ends, its distal end fixedly attached to the distal end of the non-conductive sheath; and
a control handle mounted on the proximal end of the catheter body;
wherein longitudinal movement of the puller cable relative to the catheter body results in radial expansion of the spines of the anchoring device.

24. A catheter according to claim 23, wherein each spine has the same length.

25. A catheter according to claim 23, wherein each spine has the same width.

26. A catheter according to claim 23, further comprising a stabilizing device comprising a plurality of spines formed by cutting longitudinal slits about a circumference of the distal end of the non-conductive sheath at a location on the sheath proximal the anchoring device, wherein longitudinal movement of the puller cable relative to the catheter body results in radial expansion of the spines of the stabilizing device.

27. A catheter according to claim 26, wherein the spines of the stabilizing device are longer than the spines of the anchoring device.

28. A catheter according to claim 26, wherein the spines of the stabilizing device have the same length.

29. A catheter according to claim 26, wherein the spines of the stabilizing device have the same width.

30. A catheter according to claim 23, further comprising means for deflecting the distal end of the catheter body, the means for deflecting comprising a puller wire having a proximal end and a distal end, the proximal end of the puller wire being fixedly attached in the control handle, and the distal end of the puller wire is fixedly attached to the distal end of the catheter body, whereby longitudinal movement of puller wire results in deflection of the distal end of the catheter.

31. A catheter according to claim 23, further comprising an electromagnetic sensor mounted in the distal end of the catheter body.

32. A catheter comprising:
an elongated catheter body having proximal and distal ends and at least one lumen extending therethrough;
a non-conductive sheath mounted in surrounding relation to the catheter body, wherein the non-conductive sheath is fixedly attached to the catheter body except at a distal end of the non-conductive sheath;
an anchoring device comprising a plurality of spines formed by cutting longitudinal slits about a circumference of the distal end of the non-conductive sheath;
a stabilizing device comprising a plurality of spines formed by cutting longitudinal slits about a circumference of the distal end of the non-conductive sheath at a location proximal the anchoring device;
a puller cable having proximal and distal ends, its distal end fixedly attached to the distal end of the non-conductive sheath; and
a control handle mounted on the proximal end of the catheter body;
wherein longitudinal movement of the puller cable relative to the catheter body results in radial expansion of the spines of the anchoring and stabilizing devices.

\* \* \* \* \*